(12) United States Patent
Radmand

(10) Patent No.: US 11,234,638 B2
(45) Date of Patent: *Feb. 1, 2022

(54) INTRA-ORAL ELECTROENCEPHALOGRAPHY DEVICE AND METHOD

(71) Applicant: Achaemenid, LLC, Stratford, CT (US)

(72) Inventor: Reza Radmand, Boston, MA (US)

(73) Assignee: Achaemenid, LLC, Stratford, CT (US)

( * ) Notice: Subject to any disclaimer, the term of this patent is extended or adjusted under 35 U.S.C. 154(b) by 333 days.

This patent is subject to a terminal disclaimer.

(21) Appl. No.: 16/673,077

(22) Filed: Nov. 4, 2019

(65) Prior Publication Data

US 2020/0060611 A1    Feb. 27, 2020

Related U.S. Application Data

(63) Continuation-in-part of application No. 16/202,204, filed on Nov. 28, 2018, now Pat. No. 11,000,405, (Continued)

(51) Int. Cl.
    *A61F 5/56* (2006.01)
    *A61N 1/36* (2006.01)
    (Continued)

(52) U.S. Cl.
    CPC ............ *A61B 5/4818* (2013.01); *A61B 5/369* (2021.01); *A61B 5/682* (2013.01); *A61F 5/566* (2013.01);
    (Continued)

(58) Field of Classification Search
    CPC ... A61F 5/566; A61N 1/0548; A61N 1/36139; A61N 1/3611; A61N 1/36146;
    (Continued)

(56) References Cited

U.S. PATENT DOCUMENTS 3,599,629 A    8/1971  Gordy
4,629,424 A   12/1986  Lauks et al.
(Continued)

FOREIGN PATENT DOCUMENTS

AU    2002100414 B4    11/2002
CN       1823691 A      8/2006
(Continued)

OTHER PUBLICATIONS

US 10,350,107 B2, 07/2019, Kopelman (withdrawn)
(Continued)

*Primary Examiner* — Tarla R Patel
(74) *Attorney, Agent, or Firm* — Moyles IP, LLC

(57) ABSTRACT

An oral appliance for the treatment of sleep disorders, such as obstructive sleep apnea, in a user is presented. The oral appliance may include a mouthpiece configured to receive a user's dentition. The mouthpiece may include an oxygen sensor, a pressure sensor, an airflow sensor, an actigraphy sensor, a noise detector, and at least one stimulator for providing stimulation to a user's tongue in the event of decreased oxygen saturation levels, increased pressure applied to occlusal surfaces of the user's dentition, decreased actual airflow levels and/or increased noise levels. The mouthpiece or a separate portion of the mouthpiece may be provided with an EEG sensor to determine sleep state based on EEG rhythms. The mouthpiece may be provided with pharmaceutical compound reservoirs that deliver pharmaceutical compounds to the oral mucosa of the user, which compounds treat symptoms of sleep apnea. The mouthpiece may further include a microprocessor that receives data from the oxygen sensor, pressure sensor, airflow sensor, actigraphy sensor and noise detector, and activates the at least one stimulator and/or pharmaceutical compound reservoirs.

20 Claims, 7 Drawing Sheets

Related U.S. Application Data which is a continuation-in-part of application No. 15/479,737, filed on Apr. 5, 2017, now Pat. No. 10,470,921.

(60) Provisional application No. 62/319,443, filed on Apr. 7, 2016.

(51) Int. Cl.
| | |
|---|---|
| A61B 5/1455 | (2006.01) |
| A61B 5/08 | (2006.01) |
| A61B 5/00 | (2006.01) |
| A61N 1/05 | (2006.01) |
| A61N 1/08 | (2006.01) |
| A61N 1/04 | (2006.01) |
| A61B 5/369 | (2021.01) |

(52) U.S. Cl.
CPC ......... *A61N 1/0448* (2013.01); *A61N 1/0548* (2013.01)

(58) Field of Classification Search
CPC .... A61N 1/36078; A61N 1/3601; A61N 1/08; A61N 1/0432; A61N 1/0424; A61N 1/0416; A61N 1/0428; A61N 1/375; A61N 1/0412; A61N 1/36003; A61N 1/36031; A61N 1/0448; A61B 5/0816; A61B 5/14552; A61B 5/4806; A61B 5/02416; A61B 5/228; A61B 5/4818; A61B 5/682; A61B 5/4557; A61B 5/0826; A61B 5/11; A61B 5/0823; A61B 5/087; A61B 5/4848; A61M 2205/054; A61M 2202/06; A61M 2230/205; A61M 2205/3375; A61M 2205/3344; A61M 2205/50; A61M 2205/8206; A61M 2202/04; A61M 2210/0625; A61M 31/002

See application file for complete search history.

(56) References Cited

U.S. PATENT DOCUMENTS

| | | | |
|---|---|---|---|
| 4,777,954 | A | 10/1988 | Keusch et al. |
| 5,190,053 | A | 3/1993 | Meer |
| 5,212,476 | A | 5/1993 | Maloney |
| 5,284,161 | A | 2/1994 | Karell |
| 5,490,520 | A | 2/1996 | Schaefer et al. |
| 5,765,563 | A | 6/1998 | Vander Schaaf |
| 5,792,067 | A | 8/1998 | Karell |
| 6,212,435 | B1 | 4/2001 | Lattner et al. |
| 6,418,933 | B1 | 7/2002 | Strong |
| 6,471,716 | B1 | 10/2002 | Pecukonis |
| 6,536,439 | B1 | 3/2003 | Palmisano |
| 6,598,006 | B1 | 7/2003 | Honda et al. |
| 6,604,527 | B1 | 8/2003 | Palmisano |
| 7,216,648 | B2 | 5/2007 | Nelson et al. |
| 7,690,378 | B1 | 4/2010 | Turcott |
| 7,711,438 | B2 | 5/2010 | Lattner et al. |
| 7,885,708 | B2 | 2/2011 | Shanks et al. |
| 8,751,005 | B2 | 6/2014 | Meadows et al. |
| D718,448 | S | 11/2014 | Bedford et al. |
| D718,449 | S | 11/2014 | Bedford et al. |
| 10,195,426 | B2 | 2/2019 | Kent et al. |
| 10,195,427 | B2 | 2/2019 | Kent et al. |
| 10,376,202 | B2 | 8/2019 | Shah et al. |
| 10,376,210 | B2 | 8/2019 | Paris et al. |
| 10,420,672 | B2 | 9/2019 | Hermanson et al. |
| 10,470,921 | B2 * | 11/2019 | Radmand .............. A61B 5/0816 |
| 2005/0113654 | A1 | 5/2005 | Weber et al. |
| 2006/0207611 | A1 | 9/2006 | Anonsen |
| 2007/0046461 | A1 | 3/2007 | Radmand |
| 2007/0173893 | A1 | 7/2007 | Pitts |
| 2008/0233541 | A1 | 9/2008 | Vreese et al. |
| 2008/0300469 | A1 | 12/2008 | Kuo et al. |
| 2009/0082839 | A1 | 3/2009 | Lindquist et al. |
| 2009/0210032 | A1 | 8/2009 | Beiski et al. |
| 2009/0281433 | A1 | 11/2009 | Saadat et al. |
| 2010/0204614 | A1 | 8/2010 | Lindquist et al. |
| 2010/0204747 | A1 | 8/2010 | Lindquist et al. |
| 2011/0213216 | A1 | 9/2011 | McKenna et al. |
| 2013/0109932 | A1 | 5/2013 | Saadat et al. |
| 2013/0211270 | A1 | 8/2013 | St. Laurent et al. |
| 2013/0253286 | A1 | 9/2013 | Fridman |
| 2014/0114165 | A1 | 4/2014 | Walker et al. |
| 2014/0135868 | A1 | 5/2014 | Bashyam |
| 2014/0190490 | A1 | 7/2014 | Walker et al. |
| 2014/0323839 | A1 | 10/2014 | McCreery |
| 2015/0190630 | A1 | 7/2015 | Kent et al. |
| 2015/0217115 | A1 | 8/2015 | Avitall |
| 2016/0199215 | A1 | 7/2016 | Kopelman |
| 2017/0196727 | A1 | 7/2017 | Giridharagopalan |
| 2018/0000563 | A1 | 1/2018 | Shanjani et al. |
| 2018/0015282 | A1 | 1/2018 | Waner et al. |
| 2018/0035932 | A1 | 2/2018 | Massova |
| 2018/0116863 | A1 | 5/2018 | Shah et al. |
| 2018/0177570 | A1 | 6/2018 | Alauddin et al. |
| 2019/0029587 | A1 | 1/2019 | Walker et al. |
| 2019/0057700 | A1 | 2/2019 | Kent et al. |
| 2019/0133730 | A1 | 5/2019 | Adams et al. |
| 2019/0343456 | A1 | 11/2019 | Kahlert et al. |

FOREIGN PATENT DOCUMENTS

| | | | |
|---|---|---|---|
| CN | 104921833 | A | 9/2015 |
| EP | 3318216 | B1 | 2/2020 |
| JP | 2018000930 | A | 1/2018 |
| KR | 101645870 | B1 | 8/2016 |
| KR | 20160095425 | A | 8/2016 |
| WO | 2008048649 | A2 | 4/2008 |
| WO | 2012027648 | A2 | 3/2012 |
| WO | 2012027648 | A3 | 8/2012 |
| WO | 2016087813 | A1 | 6/2016 |
| WO | 2014107446 | A1 | 7/2017 |
| WO | 2018115082 | A1 | 6/2018 |

OTHER PUBLICATIONS

United States Patent and Trademark Office; Non-Final Office Action for U.S. Appl. No. 16/781,417; dated Jul. 14, 2021; 15 pages.

United States Patent and Trademark Office; Notice of Allowance for U.S. Appl. No. 16/593,046; dated Sep. 28, 2021; 9 pages.

International Searching Authority, International Search Report and Written Opinion of PCT App. No PCT/US20/16597, dated Apr. 27, 2020, 16 pgs.

United States Patent and Trademark Office, Office Action of U.S. Appl. No. 16/781,417, dated Apr. 16, 2020, 14 pgs.

European Respiratory Journal, Severity of obstructive sleep apnoea/hypopnoea syndrome and subsequent waking EEG spectral power, vol. 32, No. 3, Jun. 5, 2012, 6 pgs., https://erj.ersjournals.com/content/32/3/705. short.

Very Well Health, Electronic Tongue Device for Sleep Apnea, dated Apr. 29, 2019, 4 pgs., https://www.verywellhealth.com/hypoglossal-nerve-stimulator-for-treating-sleep-apnea-3015195.

National Institute of Health Public Access Author Manuscript, EEG Recording and Analysis for Sleep Research, Oct. 2009, 21 pgs., https://www.ncbi.nlm.nih.gov/pmc/articles/PMC2824445/.

International Searching Authority, Written Opinion of PCT Publication No. WO2014107466, dated Mar. 19, 2014, 4 pages.

Castaneda, et al.; A review on wearable photoplethysmography sensors and their potential future application in health care; International Journal of Biosensors & Bioelectronics; dated Mar. 20, 2019; 19 pages.

United States Patent and Trademark Office; Final Office Action for U.S. Appl. No. 16/781,417; dated Nov. 17, 2020; 17 pages.

Bridgman et al., Mechanical Safety of Embedded Electronics for In-body Wearables: A Smart Mouthguard Study, dated Apr. 25, 2019, 36 pgs.

(56) References Cited

OTHER PUBLICATIONS

Silva et al., Development and Implementation of an Intraoral Device for Occlusal Stability during Sports Performance: A Case Report, dated Nov. 8, 2018, 28 pgs.

SPORTTECHIE, Pilot Program Has Select NFL Teams Wearing Sensor-Laden Mouth Guards to Study Concussions, Aug. 28, 2019, 3 pgs., https://www.sporttechie.com/nfl-mouth-guard-sensors-concussion-technology.

True Wearables, Oxxiom—Expand Your Limits Control What You Can Measure Aim Higher, 2015, 5 pgs., https://www.truewearables.com/.

United States Patent and Trademark Office, Office Action of U.S. Appl. No. 16/152,778, dated Sep. 14, 2020, 9 pgs.

United States Patent and Trademark Office; Advisory Action Before the Filing of an Appeal Brief for U.S. Appl. No. 16/781,417; dated Feb. 3, 2021; 3 pages.

United States Patent and Trademark Office; Notice of Allowance for U.S. Appl. No. 16/202,204; dated Mar. 15, 2021; 10 pages.

Lizette Borreli, Sleep Apnea May Increase Pneumonia Risk; CPAP May Increase Pulmonary Aspiration, Bacteria, Medical Daily, Mar. 3, 2014, 10 pages, http://www.medicaldaily.com/.

Tekscan, Inc., Measure Force with FlexiForce Force Sensors, 8 pages, Apr. 12, 2015, https://www.tekscan.com/product-group/embedded-sensing/force-sensors.

Arie Oliven, Treating Obstructive Sleep Apnea With Hypoglossal Nerve Stimulation, Medscape, Nov. 8, 2011, 9 pages, http://search.medscape.com/search/?q=Arie%20Oliven.

Wolkove, Norman et al., Long-term compliance with continuous positive airway pressure in patients with obstructive sleep apnea, Oct. 2008, 8 pages, www.ncbi.nlm.nih.gov/.

Wikipedia, Pulse Oximetry, Wikipedia, Oct. 1, 2004, 9 pages, https://en.wikipedia.org/wiki/Pulse_oximetry.

Nyxoah, Enjoy the comfort of Restful Nights, What is OSA?, Aug. 27, 2016, 3 pages, http://www.nyxoah.com/patients/what-is-osa.

Nyxoah, Sleep Apnea, Nyxoah, 2015, 5 pages, http://www.nyxoah.com/sleep-apnea.

Researchgate, Sublingual electrical stimulation of the tongue during wakefulness and sleep, Sep. 2001, 1 page, https://www.researchgate.net/publication/11839659.

\* cited by examiner

INTRA-ORAL ELECTROENCEPHALOGRAPHY DEVICE AND METHOD

CROSS-REFERENCE TO RELATED APPLICATIONS

This application is a Continuation-in-Part of U.S. application Ser. No. 16/202,204 filed Nov. 28, 2018, which is a Continuation-in-Part of U.S. application Ser. No. 15/479,737 filed Apr. 5, 2017, which claims the benefit of U.S. Provisional No. 62/319,443 filed Apr. 7, 2016. Each of these applications are incorporated herein by reference in its entirety.

BACKGROUND

Sleep apnea is a common medical condition during which a person experiences one or more pauses in breathing, and in some instances, experiences shallow breaths during sleep. While there are several types of sleep apnea, the most common type is obstructive sleep apnea. In this medical condition, one or more of the person's throat muscles relax during sleep causing surrounding tissues in the posterior portions of the mouth, nose and throat to collapse, thereby creating a pharyngeal obstruction that can block the upper airway. Persons suffering from obstructive sleep apnea have inadequate oxygen exchange during sleep, which can lead to daytime fatigue, lack of concentration and mood changes. Left untreated, obstructive sleep apnea can have a significant impact on a person's health, often leading to cardiovascular, stroke and metabolic disorders.

Known methods for treatment of obstructive sleep apnea include both surgical and nonsurgical devices. A popular surgical procedure is uvulopalatopharyngoplasty, which may be performed for patients who have anatomical abnormalities that cause their obstructive sleep apnea and/or make them less likely to tolerate nonsurgical devices. Uvulopalatopharyngoplasty may be a complicated surgery, during which a portion of the soft palate is removed in an effort to prevent closure of the airway by excess tissue during sleep. A disadvantage of this procedure, however, is that the operation is often expensive and may damage throat muscles necessary for swallowing and/or cause other undesirable disorders, such as, nasal regurgitation and numbness of the lower front teeth.

To reduce this risk, various nonsurgical approaches have been employed. One such nonsurgical approach includes using standardized oral appliances to incrementally advance and/or protrude the mandible (lower jaw) relative to the maxilla (upper jaw). These standardized oral appliances, commonly referred to as a mandibular advancement device, ("MAD"), typically include upper and lower dental trays, whereby the lower dental tray is designed to advance the mandible, and hence, move the tongue forward to increase the space in the posterior part of the throat and the oropharynx, which in turn may serve to increase the flow of air during sleep. The distance (degree of advancement) required to protrude and/or reposition the mandible may be, at least in part, dependent on the severity of the individual's obstructive sleep apnea, as well as psychological variables among the users. A disadvantage of using these standard oral appliances is that they may not sufficiently provide for and/or address individualized anatomical variances, such as difference in dental arches, dentition alignment and/or jaw flexibility. Another disadvantage is that in instances where the degree of advancement is excessive, the appliance may lead to long-term temporomandibular joint ("TMJ") disorders, muscular aggravation, dentition discomfort and/or myofascial disorders. As a result, use of these standard appliances has an approximate compliance rate of 75% over a 2-year period. For a detailed study of compliance with use of MAD, see *Non-CPAP therapies in obstructive sleep apnoea: mandibular advancement device therapy*, see Eur Respir J 2012; 39: 1241-1247, which is incorporated by reference in its entirety. Thus, such oral appliances may not treat obstructive sleep apnea in a manner that prevents and/or limits impacts on a person's health.

FIG. 1 depicts a system 1 including an intraoral stimulator device 2 used for providing treatment of a sleep disorder. The intraoral stimulator device 2 is powered by a rechargeable battery and includes a housing of a hollow dental retainer wireframe or mouthguard (in the case of a bilateral configuration) or a molar teeth clip (in the case of unilateral configuration) for positioning on the lower teeth. The housing 4 includes a single pair or two pairs of bilateral electrodes 5a, 5b for positioning ventral-laterally and sublingually at the posterior to middle section under the tongue for recruiting a large section of the genioglossus muscle and base-of-tongue for stimulation to regain muscle tone during sleep. The system 1 includes an external inductive recharger sub-system 6, configured to receive electrical power from a wall outlet 7 and use the electrical power to recharge a rechargeable battery (not shown) provided in the intraoral stimulator device 2 by transferring power through electromagnetic induction.

The oral appliance 1 further includes a non-rechargeable battery-operated hand-held appliance 3 that communicates instructions to the intraoral stimulator device 2. The non-rechargeable battery-operated hand-held appliance 3 is used by the patient's sleep medicine physician to program the stimulation and to set system parameters in the intraoral stimulator device 2. The stimulation can be pre-programmed or can occur as a result of change in the user's breathing pattern, as tested by accelerometer, temperature, piezoelectric film and EMG. Alternatively, the stimulation therapy may be programmed and setup up by a physician so that the therapy begins as soon as the device is turned On and ceases when the device turns Off, without regard to changes in the user's breathing pattern. An issue with continuous stimulation is that over stimulation can lead to nerve and/or muscle fatigue/damage. Moreover, while a physician can set and/or send instructions to the intraoral stimulator, the physician cannot store and or assess the breathing and/or snoring pattern of a patient in a way that allows the physician to modify treatment as may be necessary. The lack of specialized treatment measures in individual patients with unique medical needs can be problematic, particularly because they fail to store patient behavior and/or medical data that can assist medical providers in the design and/or improvement of specialized treatment measures for individual patients. Thus, such intraoral stimulator devices may fail to treat obstructive sleep apnea in a manner that prevents and/or limits impacts on a person's health.

Other methods of treating obstructive sleep apnea include the administration of positive air pressure via a continuous positive airway pressure ("CPAP") machine. The CPAP machine is often assembled for use in combination with various face or nasal masks and may provide continuously pressurized and/or forced air during the person's sleep. A disadvantage of this assembly is that it may cause nasal and/or oral mucosal dryness due to the continuously forced air and may also cause claustrophobia due to the presence of a mask on the patient's face. As a result, use of these assemblies has an approximate compliance rate of 50% over a 5-year period. For a detailed study of compliance with use of CPAP machines, see *Long-term compliance with continuous positive airway pressure in patients with obstructive sleep apnea*, Can Respir J. 2008 October; 15(7): 365-369, which is incorporated by reference in its entirety. Another disadvantage is that standard masks are not properly adapted for a customized fit for persons with unique and/or variable facial anatomies that may be natural or created by loss of muscle tone secondary to facial paralysis and/or stroke. Ill-fitting masks may lead to leakage of air and/or inadequate air intake. In addition, the masks used with CPAP machines have been found to be a breeding ground for bacteria and fungi. Despite routine washing and cleaning measures, the bacteria and fungi on these masks can grow exponentially, and lead to infections, such as pneumonia, in the airways of persons who use them. Moreover, such assemblies may not sufficiently treat obstructive sleep apnea and may fail to promote patient compliance with the treatment method.

The aforementioned treatment techniques may not provide sufficient treatment of obstructive sleep apnea, may cause and/or promote other negative health situations for the user and may not foster compliance with treatment methods.

In view of the disadvantages associated with currently available methods and devices for treating obstructive sleep apnea, there is a need for a device and method that treats obstructive sleep apnea while storing patient behavior and/or medical data relating to a user's breathing pattern, snoring pattern and/or clenching/grinding behaviors, that can assist medical providers in the design, improvement and/or modification of specialized treatment measures for individual patients. Further, there is a need for a device and method that treats obstructive sleep apnea in a single removable oral appliance and prevents and/or limits long-term TMJ disorders, muscular aggravation and/or myofascial disorders that may occur with continued use of currently available appliances.

Electroencephalography is a technique for recording and interpreting electrical activity occurring within the brain. The EEG technique is based on the nerve cells of the brain generating electrical impulses that fluctuate in particular patterns. The pattern produced by an electroencephalograph machine, which may be recorded, is called an electroencephalogram (EEG).

Obtaining an EEG typically begins with the attachment of a number of pairs of electrodes to the subject's scalp. Each pair of electrodes sends a signal to one of several recording channels of the electroencephalograph; the signal is a measure of the voltage difference between the pair. This voltage difference can be rhythmic and shown as waves on a line graph by the recording channel. For a normal, fully conscious adult in a relaxed state, the EEG shows regularly oscillating waves known as alpha waves. Subjecting the person to excitement or startling the person results in the alpha waves being replaced by rapid irregular waves of low-voltage relative to the alpha waves. A sleeping adult's brain waves become extremely slow. This is also true for a person in a coma. Other abnormal conditions have known EEG patterns. For example, delta waves are irregular slow waves in the vicinity of an area of brain damage. Although certainly not useful in all circumstances, electroencephalography has been useful as a diagnostic aid in cases of serious head injuries, brain tumors, sleep disorders, cerebral infections, epilepsy, some degenerative diseases of the nervous system and brain death.

In a sleep lab, delta waves may be utilized to assess the depth of sleep. The stronger the delta rhythm, the deeper the sleep. Increased delta power (an increased quantity of delta wave recordings) has also been found to be associated with increased concentration on internal working memory tasks.

As noted, collection of EEG data is performed with electrodes attached to the subject's scalp. One reason for this placement is to have the electrodes as close as possible to the brain with as little intervening structure as possible. In addition, since muscle cells also generate an electrical potential, electroencephalograph machines typically try to avoid muscles intervening between the electrode and the brain.

The upper jaw is a continuous extension of the skull bone, i.e., on the underside of the brain. Thus, the roof of the mouth, is close to the underside of the brain. Thus, electrodes in intimate contact with the roof of the mouth will receive brain waves in the same manner as the scalp. Other than for bald subjects, it is not possible to really 'attach' electrodes to the scalp. This presents a problem because movement of electrodes can interfere with the quality of the received voltages.

In addition to above, there is a need for a device and method capable of determining when a user is entering or in an obstructive sleep apnea condition. Such a monitoring device and method may be coupled with active treatment regimens. That is, a determination made that the user is entering or in an obstructive sleep apnea condition may be used a trigger for the active treatment regimens.

BRIEF DESCRIPTION

According to an aspect, the present embodiments are associated with an oral appliance for treatment of sleep apnea in a user. The present embodiments may comprise a mouthpiece configured to be retained in the mouth of the user, a plurality of electrodes, a microprocessor and at least one stimulator. The mouth of the user contains oral tissue and the mouthpiece has a lingual wall and a buccal wall. A plurality of electrodes are attached to the mouthpiece and electrically connected to the microprocessor; the electrodes and microprocessor are configured to determine electroencephalograph rhythms of the user's brain. The microprocessor is configured to assess the rhythms for an immediate presence of sleep apnea in the user. The at least one stimulator is also attached to the mouthpiece and is configured to respond to the immediate presence of sleep apnea in the user by stimulating the user's genioglossus. The oral appliance mouthpiece may have an upper portion and a lower portion.

Embodiments of the disclosure are further associated with an oral appliance for treatment of sleep apnea in a user comprising a mouthpiece, a plurality of electrodes, at least one electrical stimulator, a microprocessor. The mouthpiece is configured to be retained in the mouth of the user and may have an upper portion and a lower portion, each with a lingual wall and a buccal wall. The mouth of the user has oral tissue. The plurality of electrodes are attached to the mouthpiece and the microprocessor is configured to receive signals from the electrodes such that the electrodes and microprocessor cumulatively operate as an electroencephalograph and detect electrical rhythms from the user's brain. The electrical rhythms may be indicative of an immediate presence of sleep apnea in the user. The at least one electrical stimulator is attached to the mouthpiece and microprocessor; the stimulator is configured for emitting an electrical current or field in response to the immediate presence of sleep apnea in the user based on the electrical rhythms.

BRIEF DESCRIPTION OF THE FIGURES

A more particular description will be rendered by reference to specific embodiments thereof that are illustrated in the appended drawings. Understanding that these drawings depict only typical embodiments thereof and are not therefore to be considered to be limiting of its scope, exemplary embodiments will be described and explained with additional specificity and detail through the use of the accompanying drawings in which.

Figure 1:
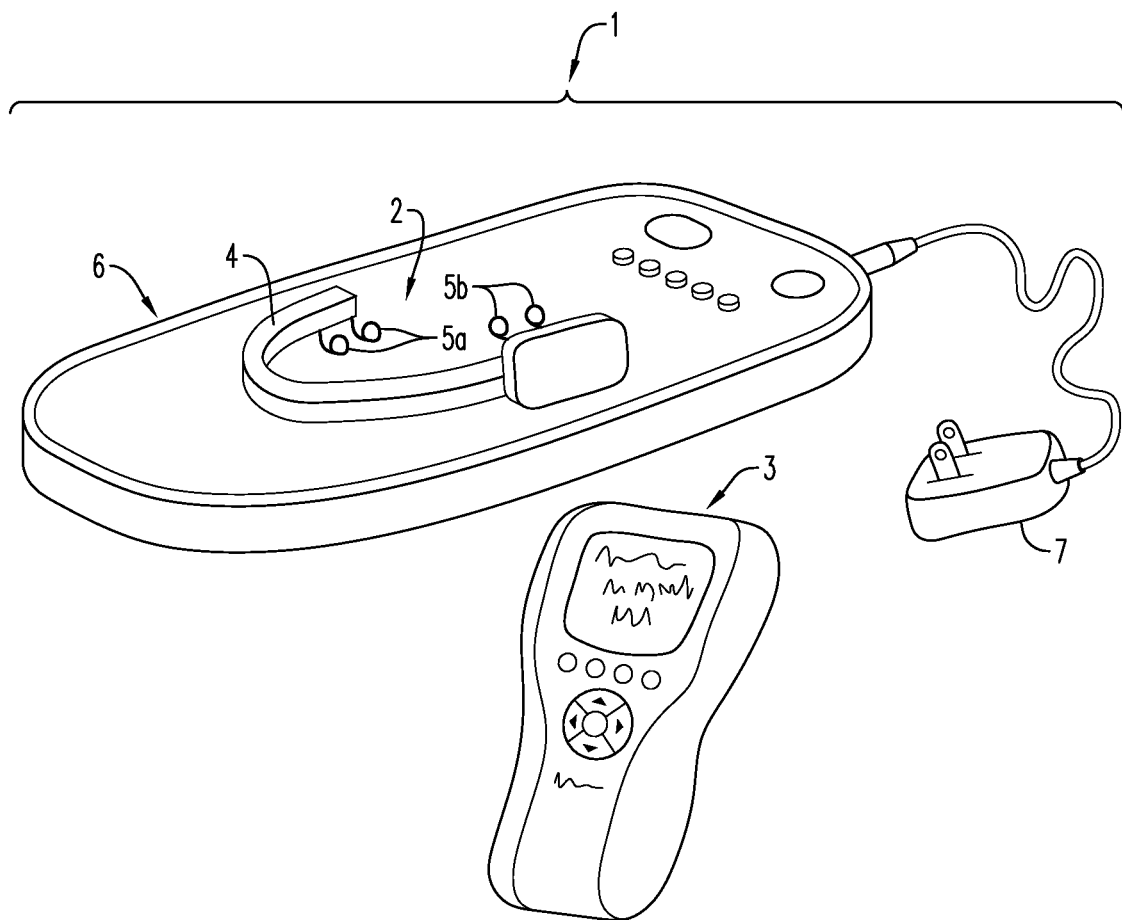
FIG. 1 is a perspective view of a prior art oral device.

Various features, aspects, and advantages of the embodiments will become more apparent from the following detailed description, along with the accompanying figures in which like numerals represent like components throughout the figures and text. The various described features are not necessarily drawn to scale but are drawn to emphasize specific features relevant to some embodiments.

DETAILED DESCRIPTION

Reference will now be made in detail to various embodiments. Each example is provided by way of explanation and is not meant as a limitation and does not constitute a definition of all possible embodiments.

Embodiments of the disclosure relate generally to devices/appliances and methods for treating obstructive sleep apnea, a device for providing electrical stimulation to a user's tongue to inhibit and/or limit snoring that may be caused by obstructive sleep apnea as well as a device including a pharmaceutical delivery reservoir for delivery of a drug for treating obstructive sleep apnea. Such devices provide particular utility in providing electrical stimulation to the user's tongue in such a manner that the stimulation does not awaken the user during sleep. Alternatively or supplemental to electrical stimulation, the device may include a pharmaceutical compound, such as an ionized medication, that treats obstructive sleep apnea. The pharmaceutical compound may be provided in a reservoir/pharmaceutical reservoir, separate from the device, or as part of the physical matrix of the device. Particularly in the former option, the reservoir may be refilled or replaced on a daily or less frequent schedule.

The oral appliance contemplated includes a mouthpiece that is configured to receive at least temporary, permanent and/or artificial lower dentition of the user. The mouthpiece may include various electronic components including one or more of the following: an oxygen sensor, a pressure sensor, an airflow sensor, a noise detector, an actigraphy sensor, a stimulator, data recorder, battery and a microprocessor. The mouthpiece may also be comprised of a material, e.g., a polymer matrix, into which a pharmaceutical compound may be incorporated for delivery to the user. Alternatively, one or more reservoirs containing a pharmaceutical compound may be attached to the mouthpiece. Each reservoir is capable of delivering a drug directly to one or more oral cavity membrane surfaces of the user. The mouthpiece may include customizable materials that provide a comfortable fit for a user while retrieving data related to the user's oxygen saturation levels, clenching and/or grinding of dentition surfaces, actual airflow levels and noise levels associated with snoring, analyzing the data, and preparing a set of instructions to the stimulator.

When utilized in combination with a pharmaceutical compound, the stimulator components may be utilized to effect transfer of the drug from the device to the oral mucosa of the user. This drug delivery function may be in addition to the electrical stimulation of a user's oral musculature or may be alternative thereto, i.e., the electrical stimulation may only function as a drug release/delivery mechanism. The stimulators may operate to rupture or pierce the pharmaceutical reservoir(s) attached to or otherwise associated with the mouthpiece upon receiving and instruction to do so. Alternatively, the stimulators may be utilized in combination with pharmaceuticals bearing an electrically charged surface, as will be further explained. In the event that the microprocessor sends a signal resulting in the rupture of pharmaceutical reservoir(s), notification of the user that the reservoir is in need of replacement can be conveyed by the microprocessor to the user. Such notification may take the form of a smartphone notification of the user or visual notification, e.g., activation of LED light when user is next able to see said light.

According to an aspect, the mouthpiece is customized to be receivably positioned and/or secured on the mandible of the user. According to an aspect, the mouthpiece is customized to receive the lower dentition of the user. In any event the mouthpiece may be customized such that it provides a comfortable fit that enhances the user's comfort and reinforces the user's likelihood of repeated wear of the mouthpiece, i.e., the user's compliance rate.

For purposes of illustrating features of the embodiments, embodiments will now be introduced and referenced throughout the disclosure. Those skilled in the art will recognize that this example is illustrative and not limiting and is provided purely for explanatory purposes.

Figure 2:
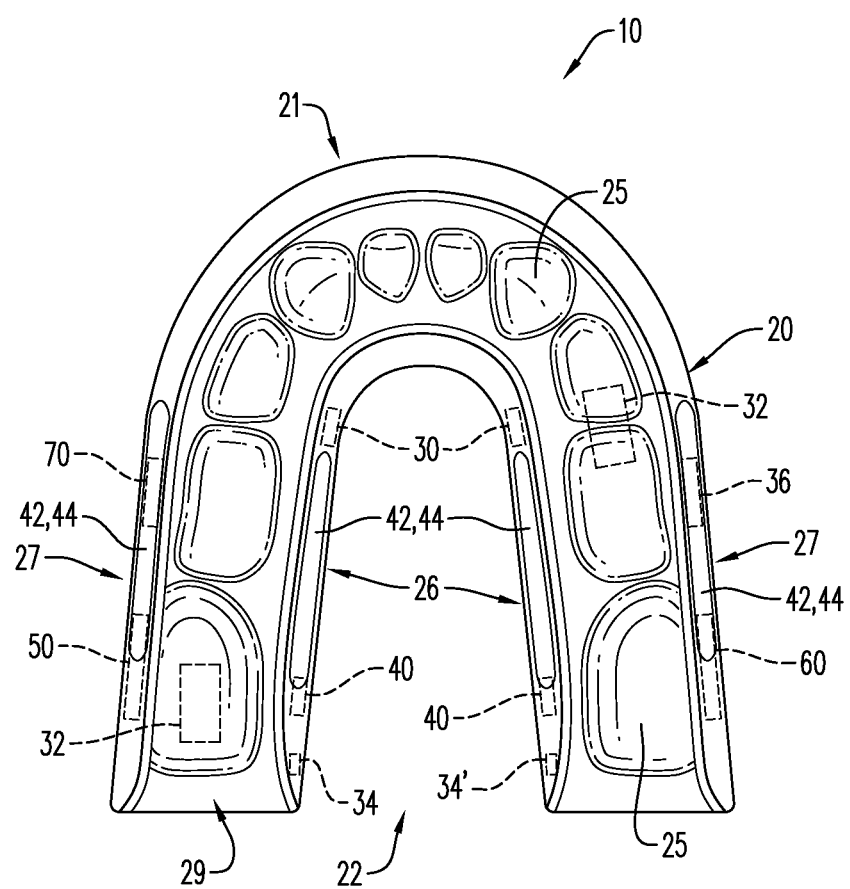
FIG. 2 is a top view of an oral appliance, according to an embodiment.
Figure 3:
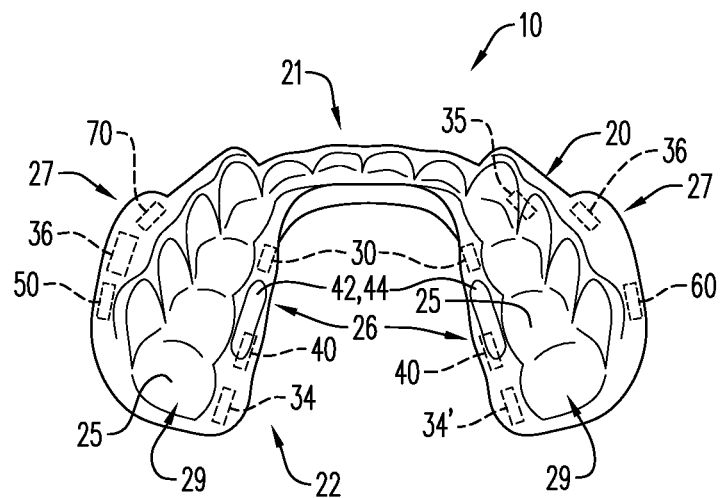
FIG. 3 is a perspective view of an oral appliance, according to an embodiment.
Figure 4:
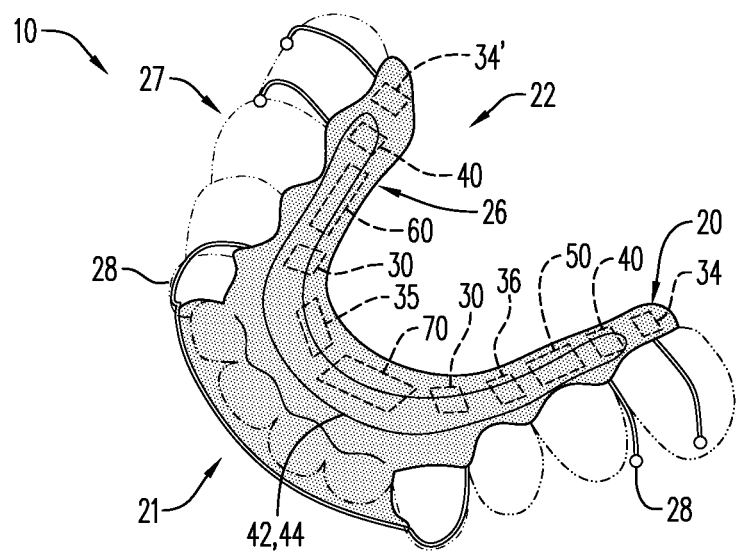
FIG. 4 is a perspective view of an oral appliance, according to an embodiment.

In an embodiment, and with particular reference to FIGS. 2-4, an oral appliance 10 for treatment of sleep apnea in a user is provided. The oral appliance 10 is illustrated as having a mouthpiece 20 and several components. In an embodiment, the mouthpiece 20 is "customizable", that is, customized to the individual user's mouth in such a manner that it provides for a comfortable fit over and around surfaces of the user's hard (teeth/dentition) and/or soft tissues (general mouth structure, including gums). When customized, the mouthpiece 20 may fit over temporary, permanent, primary natural and/or artificial lower dentition of adult and/or child users. The mouthpiece 20 may be configured to receive a removable denture of the user. According to an aspect, the mouthpiece 20 is fabricated over the lower jaw, that is, the mandible, with partial or complete absence of dentition. When customized, the mouthpiece 20 can be formed of any self-conforming material that may be adaptable to variances and/or changes in mouth structure, or through use of a dental impression of the individual user's dentition, as would be understood by a person having ordinary skill in the art. In other words, a mandibular impression and/or a dental impression can be taken, whereby a negative imprint of the user's hard and/or soft tissues are used to create a positive reproduction (or cast) customized for the user.

The types of materials selected to form the mouthpiece 20 would be known to one of ordinary skill in the art and includes polymers, thermoplastics, acrylics, silicone, rubber, metal wires or any other material that can be used to form the mouthpiece 20 conformed to the user's dentition. In an embodiment, the materials are medical-grade, latex-free, BPA-free and any other material known to minimize patient health risks. According to an aspect, the mouthpiece 20 may be formed from the impression made in a thin, resilient material. The mouthpiece material may also be selected, particularly from polymers, for its ability to have a pharmaceutical compound incorporated within the structural matrix.

In an embodiment and as illustrated in FIGS. 2 and 3, the mouthpiece 20 includes a central channel 29 bounded by a lingual portion 24 and a buccal portion 23. The central channel 29 may be configured to be receivably positioned over and/or receive one or more of the user's dentition such that the mouthpiece 20 is secured thereon. When the mouthpiece 20 is in use, the central channel 29 may receive the user's dentition and may extend over and/or cover occlusal or bite surfaces of the user's teeth. The lingual portion 24 of the mouthpiece 20 extends between the user's teeth and the user's tongue. In an embodiment and as illustrated in FIGS. 2 and 3, the buccal portion 23 of the mouthpiece 20 extends between the user's teeth and the user's cheek.

According to an aspect, the mouthpiece 20 is configured to be secured to the user's dentition. In an embodiment and as illustrated in FIG. 4, the mouthpiece 20 includes the lingual portion 24 and dentition attachment members 28 coupled to the lingual portion 24. The dentition attachment members 28, as well as the lingual portion 24, may be customizable, such that the dentition attachment members 28 have a shape and size that substantially conforms to the dentition of the user, thereby providing the user with the mouthpiece 20 having a secured and customized fit. Typically, the dentition attachment members 28 are provided in a wire-frame form, in a way that extends from the lingual portion 24 to wrap over or around the individual user's dentition and anchor the lingual portion 24 between the lingual surface of the teeth and the tongue. According to an aspect, at least a portion of the dentition attachment members 28 is shaped to form a retention loop around one or more teeth of the user.

Similar to the dentition receiving cavities 25 described for the mouthpiece 20 of FIGS. 2 and 3, the lingual portion 24 depicted in FIG. 4 may also be customized to have a shape that is substantially the same as the shape of the individual user's dentition for which it has been molded and/or shaped to fit, thereby assisting the retention function of the dentition attachment members 28. In any event, the mouthpiece 20 is capable of being at least temporarily fixed in place by virtue of having been molded and conformed to the dentition of the user and/or being provided with the dentition attachment members 28, thus providing the customized fit. As such, the mouthpiece 20 may provide a retention function thereby allowing the oral appliance 10 to remain in place during the user's sleep, particularly in situations where the user may make slight to moderate movements during sleep and/or when the user may be awake. Thus, the mouthpiece 20 may be substantially immovable unless positive effort is applied to remove the mouthpiece 20. In other words, the user may remove the mouthpiece 20 at any time, if desired, by exerting a little pressure to remove the mouthpiece 20. Since the mouthpiece 20 is not permanently affixed to the dentition, it can be worn and/or subsequently removed by the user at any time. Therefore, the oral appliance 10 may be used for varying lengths of time.

According to an aspect and as illustrated in FIGS. 2-4, the components positioned on and/or embedded within the mouthpiece 20 include one or more of the following components: an oxygen sensor 30, a pressure sensor 32, an airflow sensor 34, a noise detector 35, an actigraphy sensor 36, a stimulator 40, a pharmaceutical reservoir 42, a microprocessor 50, a data recorder 60 and a battery 70. According to an aspect, the mouthpiece 20 includes dry protective areas or covering to these electronic components that substantially inhibit and/or limit water and/or tissue damage to the components (not shown). Such dry/protected zones may be formed by virtue of the components being embedded within the mouthpiece 20 itself.

As illustrated in FIGS. 2-4, the oxygen sensor(s) 30 may be provided near an anterior portion 21 of the mouthpiece 20, i.e., towards the user's lips and away from the user's pharynx. According to an aspect, the oxygen sensor 30 is configured to monitor and/or determine actual oxygen saturation levels of the user's hemoglobin. The oxygen sensor 30 may be adapted to monitor and/determine the pulse and/or heart rate of the user. The oxygen sensor 30 may be positioned on or in the lingual portion 24 of the mouthpiece 20. In an embodiment, the oxygen sensor 30 is positioned primarily towards lateral portions of the tongue, which are generally understood to be the most vascular areas of the tongue, i.e., having numerous blood vessels, as well as the buccal regions of the upper jaw. According to an aspect, the oxygen sensor 30 is a transceiver such as a pulse oximeter configured to monitor/sense the oxygen saturation level of a user by analyzing the change in color of the user's blood. The pulse oximeter may measure the pulse rate of the user, typically in beats per minute, based on variations and/or deviations in the user's oxygen saturation level. An exemplary pulse oximeter, for example, may include light emitting diodes configured to transmit red and infrared lights to vascular surfaces of the user's tongue and sense changes in oxygen level in the user's tongue. According to an aspect, two oxygen sensors 30 are provided on the lingual portion 24 of the mouthpiece 20. The two oxygen sensors 30 may be bilaterally positioned on the mouthpiece 20. While FIGS. 2-4 illustrate two oxygen sensors 30 being positioned on the mouthpiece 20, it is to be understood that the number of oxygen sensors provided may be 3, 4, 5, 6 or more.

According to an aspect and as illustrated in FIGS. 2 and 3, the oral appliance 10 may include one or more pressure sensors 32. According to an aspect, the one or more pressure sensors 32 are configured to detect signs of clenching and/or grinding by the user that occur, for example, while the user is asleep. The pressure sensors 32 may be positioned in or on the central channel 29. In an embodiment, the pressure sensors 32 are positioned in the dentition receiving cavities 25, such that the pressure sensors 32 are positioned substantially adjacent to the user's mandibular occlusal and/or bite surfaces. According to an aspect, the pressure sensors 32 are on an exterior surface of the central channel 29, where the central channel 29 has an interior surface configured for receiving the dentition receiving cavities 25 and the exterior surface is positioned opposite of the interior surface, such that the pressure sensors 32 are positioned substantially adjacent to the user's maxillary occlusal and/or bite surfaces. In some embodiments (not shown), the pressure sensors may be provided on the dentition attachment members 28, such as those manufactured by Tekscan under the brand Flexi-Force™ Force Sensors. Such signs of clenching may include force sensors configured to measure the force that is being applied to occlusal and/or bite surfaces of the user's teeth. According to an aspect, the pressure sensors 32 are a thin resilient material. The one or more pressure sensors 32 may be electrically sealed and/or impervious to liquids, saliva and/or oral tissue. The number of pressure sensors 32 provided on the mouthpiece 20 may be selected based on the user's proclivity to grinding and/or clenching. According to an aspect, the number of pressure sensors 32 provided is 2, 3, 4, 5, 6 or more.

In an embodiment, the mouthpiece 20 includes one or more airflow sensors 34 configured to measure the actual airflow and/or breathing rate of the user, i.e., the rate of air that is inhaled and/or exhaled through the mouthpiece 20 by the user. According to an aspect, the airflow sensor 34 is configured to detect any reduction and/or cessation of airflow during sleep. The airflow sensor 34 may be arranged at any position on the mouthpiece 20 that is in a general flow path of air inhaled and/or exhaled by the user. As illustrated in FIG. 2, the airflow sensor 34 may be positioned near a posterior portion 22 of the mouthpiece 20. According to an aspect, the airflow sensor 34 is bilaterally positioned on the mouthpiece 20. As illustrated in FIGS. 2-3, one airflow sensor 34 may be positioned to the left of the lingual portion 24, while another airflow sensor 34' may be positioned to the right of the lingual portion 24. In any event, both airflow sensors 34, 34' may work in tandem to measure the user's airflow rate. Airflow sensors 34 may be arranged in/on at least one of the lingual portion 24 and the buccal portion 23 of the mouthpiece 20. The number of airflow sensors 34 provided on the mouthpiece may be selected based on the needs of the user. According to an aspect, the number of airflow sensors provided is 2, 3, 4, 5 or more.

According to an aspect and as illustrated in FIGS. 2-4, the mouthpiece 20 may include an actigraphy sensor 36 configured to monitor and capture data related to sleep activity, including sleep position and movement of the user during sleep. The actigraphy sensor 36 may embedded in or otherwise connected to the mouthpiece 20, at any desired position. According to an aspect and as illustrated in FIG. 2-3, the actigraphy sensor 36 is position at the buccal portion 23 of the mouthpiece 20. In an alternate embodiment and as illustrated in FIG. 4, the actigraphy sensor 36 may be positioned at the lingual portion 24 of the mouthpiece 20. The actigraphy sensor 36 may determine the user's sleep positions, such as, for example, a supine position during which the user is positioned on his/her back, a prone position during which the user is lying face down and/or lateral recumbent positions during which the user is lying on their left or right sides. The actigraphy sensor 36 may measure the time the user sleeps in each identified position and/or the frequency of the user changing from one sleep position to another sleep position.

The oral appliance 10 may include a noise detector 35 configured to detect actual noise and/or vibrations caused by the user's snoring. According to an aspect, the noise detector 35 is internally hard-wired to one or more components coupled to or otherwise embedded in the mouthpiece 20, such as, for example, the stimulator 40, the microprocessor 50 and the data recorder 60, such that the noise detector 40 can communicate with the components. The noise detector 35 may be configured to wirelessly communicate with at least one of the stimulator 40, the microprocessor 50 and the data recorder 60. The noise detector 35 may be positioned on or otherwise embedded in the mouthpiece 20 at any desired location. According to an aspect, the noise detector 35 is positioned at the posterior portion 22 of the mouthpiece 20, such that relevant snoring information may be detected close to a sound source, i.e., the user's pharynx. In an embodiment, the noise detector 34 is positioned at the anterior portion 21 of the mouthpiece 20. As illustrated in FIG. 3, the noise sensor 35 may be positioned at the buccal portion 23 of the mouthpiece 20. In an embodiment and as illustrated in FIG. 4, the noise sensor 35 is positioned at the lingual portion 24 of the mouthpiece 20. While FIGS. 3-4 illustrate a single noise detector 35 being provided on the mouthpiece 20, it is to be understood that 2, 3, 4 or more noise detectors 35 may be provided.

According to an aspect and as illustrated in FIGS. 2-4, the at least one stimulator 40 is provided near the posterior portion 22 of the mouthpiece 20, that is generally near the back of the user's mouth. The stimulator 40 is configured to provide a gentle stimulation to the tongue of the user, as will be described in more detail hereinbelow. In an embodiment, the stimulator 40 is positioned on the lingual portion 24 of the mouthpiece 20, adjacent to the tongue. The stimulator 40 may be bilaterally positioned on the mouthpiece 20, such that bilateral stimulation may be provided to both sides of the user's tongue. The stimulator 40 may be positioned substantially adjacent to a base of the user's tongue, for example, adjacent to the user's genioglossus muscle. Thus, the stimulator 40 may be configured for providing stimulation to the genioglossus muscle of the user's tongue in a manner that allows the muscle tone of the genioglossus muscle to be regained. Such stimulation may be electrical impulses that cause the genioglossus muscle to contract and/or cause the user to reduce the amount of force being applied to occlusal and/or bite surfaces of the user's teeth. In some embodiments, contraction of the genioglossus muscle may cause the user's tongue to protrude, thereby creating more space in the user's pharynx and helping the user breathe more easily in a manner that increases the oxygen saturation levels of the user's hemoglobin. The stimulation may be in response to the actual saturation level of hemoglobin of the user, as measured by the at least one oxygen sensor 30.

According to an aspect, the stimulator 40 is activated based on measurements received from the oxygen sensors 30, the pressure sensors 32, the airflow sensors 34 and/or the noise detector 35. The stimulator 40 may be activated if the oxygen sensor 30 determines that the actual oxygen saturation level of hemoglobin of the user is at a predetermined oxygen level, that is, that a certain oxygen level has been pre-determined to be insufficient. The stimulator 40 may provide at least intermittent stimulation to the genioglossus muscle of the user's tongue until the oxygen saturation level of hemoglobin rises above the predetermined oxygen level. In an embodiment, the stimulator 40 is activated if the oxygen sensor 30 determines that the actual oxygen saturation level of hemoglobin of the user is below about 95% oxygen saturation. Stimulation of the user's genioglossus muscle may facilitate an increase in respiratory flow to the user, thereby increasing the availability of oxygen to the user and the increase of oxygen saturation levels of hemoglobin. According to an aspect, when the oxygen sensor 30 determines that the oxygen saturation level of hemoglobin of the user is above about 95% oxygen saturation, the stimulator 40 is not activated. In an embodiment, the stimulator 40 is activated if the pressure sensors 32 detect grinding and/or clenching by the user. According to an aspect, the stimulator 40 provides stimulation until the force applied to occlusal and/or bite surfaces of the user's teeth are below a predetermined force level. The stimulator 40 may stop stimulation once the pressure sensors 32 detect that grinding and/or clenching has substantially decreased and/or ceased, as evidenced by the detected force level. According to an aspect, the stimulator 40 is activated when the airflow sensor 34 determines that the frequency of air inhaled and/or exhaled by the user is below a predetermined airflow level. In an embodiment, the stimulator 40 is activated when the airflow sensor 34 determines that airflow is at or below 30% of the user's natural airflow or breathing rate, i.e., air inhaled and/or air exhaled by the user while the user is awake (natural airflow), has been reduced by 30%. The stimulator 40 may provide stimulation to the genioglossus muscle until the predetermined airflow level is achieved and/or airflow to the user is at least about 30% of the user's natural airflow rate. In an embodiment, the stimulator 40 is activated if the noise detector 35 detects that the actual noise and/or vibrations are above a predetermined noise level. In this embodiment, the stimulator 40 provides gentle electrical stimulation to the genioglossus muscle of the user's tongue until the actual noise and/or vibrations are below the predetermined noise level.

In an embodiment, the stimulator 40 is configured to provide constant stimulation to the genioglossus muscle of the user's tongue. Alternatively, the stimulator 40 may provide variant stimulation to the genioglossus muscle of the user's tongue. The variant stimulation may increasingly stimulate the genioglossus muscle of the tongue until the oxygen saturation level is at the predetermined oxygen level, such as, for example, at or above 95%. In an embodiment, the variant stimulation increasingly stimulates the genioglossus muscle until the force applied to the occlusal and/or bite surfaces is below the predetermined force level. The variant stimulation provided by the stimulator 40 to may increasingly stimulate the genioglossus muscle until the predetermined airflow level is achieved and/or until the actual noise and/or vibrations are below the predetermined noise level. According to an aspect, the strength and frequency of the electrical impulses in variant mode will depend on how quickly the oxygen saturation of hemoglobin and/or the predetermined force level is achieved. The constant or variant stimulation may be a gentle stimulation that does not disturb and/or awaken the user during sleep. According to an aspect, the constant or variant stimulation is gentle enough so that the user does not recognize it when wearing it when the user is at least slightly awake. The stimulator 40 may alternate between a constant stimulation mode and a variant stimulation mode. In an embodiment, the at least one stimulator 40 is an electrode configured to provide gentle electrical impulses. The gentle electrical impulses may be provided to the genioglossus muscle of the user's tongue in a non-invasive manner and in such a manner that stimulation does not awaken the user during sleep.

In an embodiment, the mouthpiece 20 or structures associated with the mouthpiece 20 allow delivery of a pharmaceutical compound to foster retention or reacquisition of muscle tone of the genioglossus muscle. Such a pharmaceutical compound may cause the genioglossus muscle to contract. Activation of the genioglossus muscle may be achieved utilizing cholinergic drugs such as neostigmine. Other stimulants and/or drugs that activate and/or increase calcium ion release/activation affecting muscle contraction may also be used to activate the genioglossus muscle, such compounds include norepinephrine and caffeine.

In another embodiment, genetically engineered light stimulation of the nerves and muscles, specific to the desired site, may be utilized. This concept is called optogenetics. Optogenetics makes it possible to stimulate neurons with light by inserting the gene for a protein called channelrhodopsin-2, from green algae. When a modified neuron is exposed to blue light, the protein initiates electrical activity inside the cell that then spreads from neuron to neuron. The optical control method provides advantages over electrical stimulation for muscle and the biomechanics of human movement. That is, photons are released by the mouthpiece 20 instead of electrical charge/current.

In an embodiment, the pharmaceutical compound may be incorporated into the material of mouthpiece 20 for active or passive release. Passive release may be triggered by environmental factors in the users mouth such as change in temperature, pH or similar variables. Active release may involve electrical stimulation controlled by the microprocessor 50 responsive to inputs from one or more of the sensors associated with mouthpiece 50. Electrical stimulation resulting in drug release is discussed further below.

Iontophoresis is a drug delivery process utilizing a voltage gradient. Molecules are transported through a semipermeable material or barrier by electrophoresis and/or electroosmosis. Electrophoresis is the motion of charged particles, ions or anions, in the presence of an electric field. Particles bearing a surface charge present in a liquid or gel, i.e., capable of substantial movement relative to the medium in which they are contained, are most amenable to electrophoresis, though movement through other materials is possible. Electroosmosis is the motion of liquid induced by an applied electrical potential across a porous material, capillary tube, membrane, microchannel, or any other fluid conduit. Iontophoresis is an active transport of matter resulting from an applied electric current. Such transport is measured in units of chemical flux, commonly $\mu mol/(cm^2*hour)$.

The material chosen for mouthpiece 20 may be, for example, a polymer acting as a semipermeable retainer of a selected pharmaceutical compound. That is, the material of mouthpiece 20 will retain the pharmaceutical compound under storage and other conditions while releasing the pharmaceutical compound under certain passive or active conditions. In the case of active release, an electric charge or electric field may be applied to some portion of mouthpiece 20, causing the pharmaceutical compound to flow out of the mouthpiece 20 and be made available for absorption through the user's oral mucosa precisely to the tissues to which it is designed to treat. Whether released actively or passively, once a reservoir 42 is empty, notification of the user that a reservoir 42 is in need of replacement can be conveyed by the microprocessor 50 to the user. Such notification may take the form of a smartphone notification of the user or visual notification, e.g., activation of LED light when user is next able to see said light. Replacement reservoir(s) 42 may be provided to user and have means, e.g., friction or adhesive (e.g., pressure sensitive adhesives/PSA), for attachment to mouthpiece 20 upon notification of the user regarding the need for replacement.

In an embodiment, a reservoir 42 containing a liquid, gel or similar state of matter may be associated with the mouthpiece 20. For example, the reservoir 42 may comprise a pouch attached to a surface of mouthpiece 20 and containing a pharmaceutical compound. In an embodiment, the pouch is formed from a material that will rupture when subjected to an electric charge or field by activation of stimulator 40. This activation may be the result of microprocessor 31 responding to input from one or more sensors, as described previously. The reservoir 42 pouch will typically be attached to mouthpiece 20 at a surface unlikely to bear much force associated with the user's teeth biting or rubbing against one another or the mouthpiece 10. Thus, the lingual wall 26 or buccal wall 27 are ideal for placement of reservoir(s) 42. The reservoir 42 may be removed after use or simply dissolve during use; either way, placement of a new reservoir 42 immediately prior to insertion of the mouthpiece 20 by the user can be done when needed.

In an embodiment, the material of the pouch walls 44 forming reservoir(s) 42 may be a semipermeable polymer through which the pharmaceutical compound may pass under specified passive conditions or one through which the pharmaceutical may pass when an electrical stimulus or field is applied to the pouch reservoir 42. When electrical stimulus is required for iontophoresis, besides considerations of reservoir 42 placement discussed above, it is also important to consider placement relative to electrical stimulator(s) 40. A feature of the stimulating reservoir(s) 42 to dispense the pharmaceutical compound is that delivery of the compound may be initiated, halted and reinitiated according to readings sensors 30, 32, 34 and/or 36 convey to microprocessor 50. Thus, instead of having the pharmaceutical compound delivered as a bollus, it may be delivered closer to the profile of user's need.

Another semi-permeable barrier through which molecules of the pharmaceutical compound may be transported is the outermost layer of human skin, i.e., the stratum corneum and other oral mucosa layers. Thus, however released from mouthpiece 20, the pharmaceutical compound is absorbed by the oral mucosa of the user. In some embodiments, pharmaceutically induced contraction of the genioglossus muscle may cause the user's tongue to protrude, thereby creating more space in the user's pharynx and helping the user breathe more easily in a manner that increases the oxygen saturation levels of the user's hemoglobin. The stimulation may be in response to the actual saturation level of hemoglobin of the user, as measured by the at least one oxygen sensor 30. Release of the pharmaceutical compound resulting in stimulation to the genioglossus muscle of the user's tongue may continue until the oxygen saturation level of hemoglobin rises above the predetermined oxygen level. In an embodiment, the stimulator 40 is activated if the oxygen sensor 30 determines that the actual oxygen saturation level of hemoglobin of the user is below about 95% oxygen saturation. Stimulation of the user's genioglossus muscle may facilitate an increase in respiratory flow to the user, thereby increasing the availability of oxygen to the user and the increase of oxygen saturation levels of hemoglobin. According to an aspect, if the oxygen sensor 30 determines that the oxygen saturation level of hemoglobin of the user is above about 95% oxygen saturation, stimulator 40 is not activated and reservoir 42 is not caused to dispense the pharmaceutical compound through iontophoresis or otherwise. In an embodiment, the stimulator 40 is activated if the pressure sensors 32 detect grinding and/or clenching by the user. According to an aspect, the stimulator 40 provides electrical stimulus or an electrical field to reservoir(s) 42 as instructed by microprocessor 50 acting in response to inputs from one or more of sensors 30, 32, 34 and 36.

As illustrated in FIGS. 2-4, a microprocessor 50 may be provided on and/or embedded within the mouthpiece 20. As illustrated in FIGS. 2 and 3, the microprocessor 50 may be positioned on or in the buccal portion 23. Alternatively, and as illustrated in FIG. 4, the microprocessor 50 may be positioned on or in the lingual portion 24 of the mouthpiece 20. In other words, it is possible to place the microprocessor 50 on the mouthpiece 20 wherever available real estate may be found. Thus, when more than one component, such as, for example, the oxygen sensor 30 and the stimulator 40, are positioned at the lingual portion 24 of the mouthpiece 20, the microprocessor 50 may be positioned away from these regions on the buccal portion 23. In some embodiments and as illustrated in FIG. 4, the microprocessor 50 is positioned at the lingual portion 24 of the mouthpiece 20 and may be embedded therein. It is to be understood that the microprocessor 50 may be positioned at any location that enables it to communicate with the components included in the oral appliance 10, such as, for example, the oxygen sensor 30, the pressure sensor 32, the airflow sensor 34, the noise detector 35, the actigraphy sensor 36, the stimulator 40, the data recorder 60, and/or a battery 70, while ensuring that the location of the microprocessor 50 helps maintain a comfortable fit and/or maintain wearability of the mouthpiece 20 by the user. The microprocessor 50 may be attached to and/or positioned at any desired location on the mouthpiece 20, such as, anteriorly, posteriorly and any location therebetween. According to an aspect, the microprocessor 50 is sized and/or positioned to provide for a comfortable fit for the user. To be sure, the microprocessor 50 may be positioned at any location that does not interfere with the comfortable fit of the mouthpiece 20 for the user. The microprocessor 50 may be configured to receive data corresponding to the actual oxygen saturation levels of hemoglobin from the at least one oxygen sensor 30, and data relating to the user's grinding and/or clenching behavior, actual airflow levels, actual noise and/or snoring levels. In an embodiment, the microprocessor 50 is configured to activate the stimulator 40 if the oxygen sensor 30 determines that the actual oxygen saturation level of hemoglobin of the user is at a predetermined level. According to an aspect, the microprocessor 50 activates the stimulator 40 if the pressure sensor 32 determines that the user is clenching and/or grinding his/her dentition at unacceptable levels. The microprocessor 50 may activate the stimulator 40 if the airflow sensor 34 determines that the user's airflow rate is below the predetermined airflow level. According to an aspect, the microprocessor 50 activates the stimulator 40 if the noise detector 35 determines that the user's actual noise and/or vibrations during sleep are above the predetermined noise level.

As illustrated in FIGS. 2-4 and in an embodiment, the oral appliance 10 includes a data recorder 60. The data recorder 60 may be positioned at, for instance, the buccal portion 23 of the mouthpiece 20, (see, for instance, FIG. 2). According to an aspect and as illustrated in FIG. 3, the data recorder 60 is positioned at the lingual portion 24 of the mouthpiece 20. In an embodiment, the data recorder 60 is configured to receive and/or store information provided from the microprocessor 50. According to an aspect, the data recorder 60 receives and/or stores the actual oxygen saturation level of hemoglobin, the predetermined force level of the user applied to the occlusal and/or bite surfaces and/or the predetermined airflow level, as provided by the oxygen sensor 30, the pressure sensors 32 and the airflow sensor 34, respectively. The data recorder 60 may also receive and/or store stimulation information regarding the quantity and/or frequency of stimulations provided by the stimulator 40. The data recorder 60 may also store pharmaceutical compound dispensing information such as the volume/dosage of pharmaceutical dispensed from reservoir(s) 42 at each dispensing event and the total volume dispensed and, thus, remaining in reservoir(s) 42. This remaining pharmaceutical compound data may be used in signaling user as to replacement of reservoir(s) 42.

According to an aspect, the appliance 10 includes a transceiver (not shown). The transceiver may be configured to remotely monitor any additional components provided on and/or within the mouthpiece 20. In an embodiment, the transceiver may be configured for use with a customized web-based application for a handheld wireless communication device. The customized web-based application may include features such as, a graph of the user's sleep position and chart and/or graphical data related to oxygen saturation levels of hemoglobin and the pressure applied to occlusal surfaces of the user's dentition. According to an aspect, the customized web-based application may include data related to the user's heart rate. In an embodiment, the transceiver communicates with handheld wireless communication devices having Bluetooth® capabilities. The transceiver may be communicable with handheld wireless communication devices, such as, for example, computers, smart watches, smart phones, and the like.

The oral appliance 10 may include a battery 70. While it is contemplated that the battery 70 is rechargeable, it may be disposable. The battery 70 may be configured to provide power to at least one of the oxygen sensor 30, the pressure sensor 32, the airflow sensor 34, the noise detector 35, the actigraphy sensor 36, the stimulator 40, the microprocessor 50, the data recorder 60 and the transceiver. According to an aspect, the battery 70 includes an energy store and a contact element sealably arranged on the mouthpiece 20 (not shown). In an embodiment, the battery 70 is embedded within the mouthpiece 20, such that the battery 70 is not exposed to liquids, saliva and/or oral tissue. The battery 70 may be positioned near the buccal portion 23 (see, for instance, FIG. 2). According to an aspect, the battery 70 is positioned near the lingual portion 24 (see, for instance FIG. 4) of the mouthpiece 20.

Figure 5:
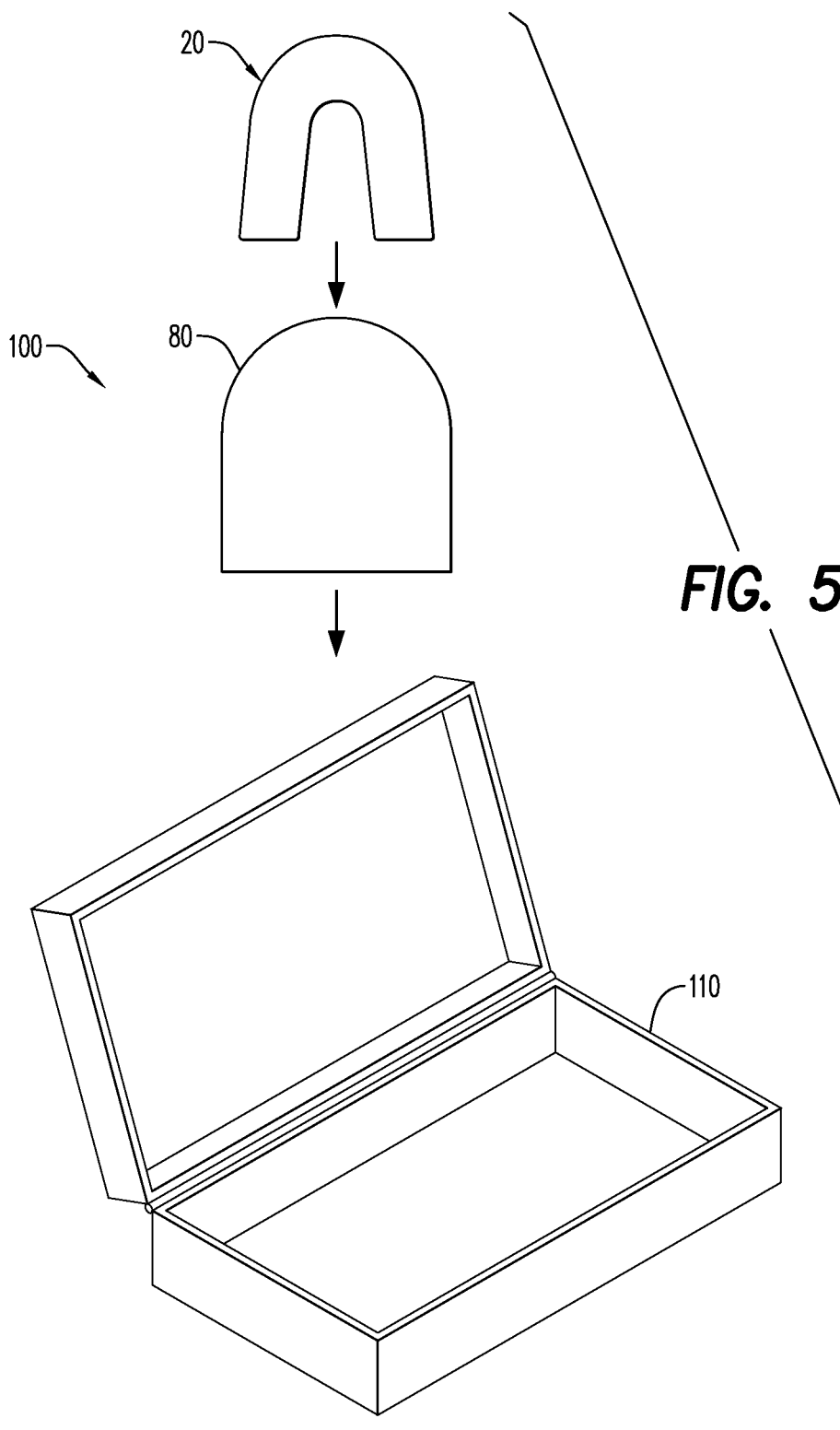
FIG. 5 is a perspective view of an oral appliance kit, according to an embodiment.

As illustrated in FIG. 5, the oral appliance may include a data transfer pod 80. The data transfer pod 80 may be configured to charge and/or provide power to the rechargeable battery 70. According to an aspect the data transfer pod 80 is configured to retrieve and/or store information collection by the data recorder 60, such that the user and or medical provider can track and/or assess the collected information. According to an aspect, the transceiver may include power amplifiers (not shown) configured to reduce power requirements of the oral appliance 10, thereby helping to conserve life of the rechargeable battery 70. The data transfer pod 80 may be provided with an electrical contact component accessible to a plug of a power supply unit (not shown).

As illustrate in FIG. 5 and in an embodiment, an oral appliance kit 100 for treatment of sleep apnea in a user is provided. In an embodiment, the oral appliance kit 100 includes the oral appliance 10, including the various electronic components, as substantially described above and illustrated in FIGS. 2-4, and the data transfer pod 80.

Figure 6:
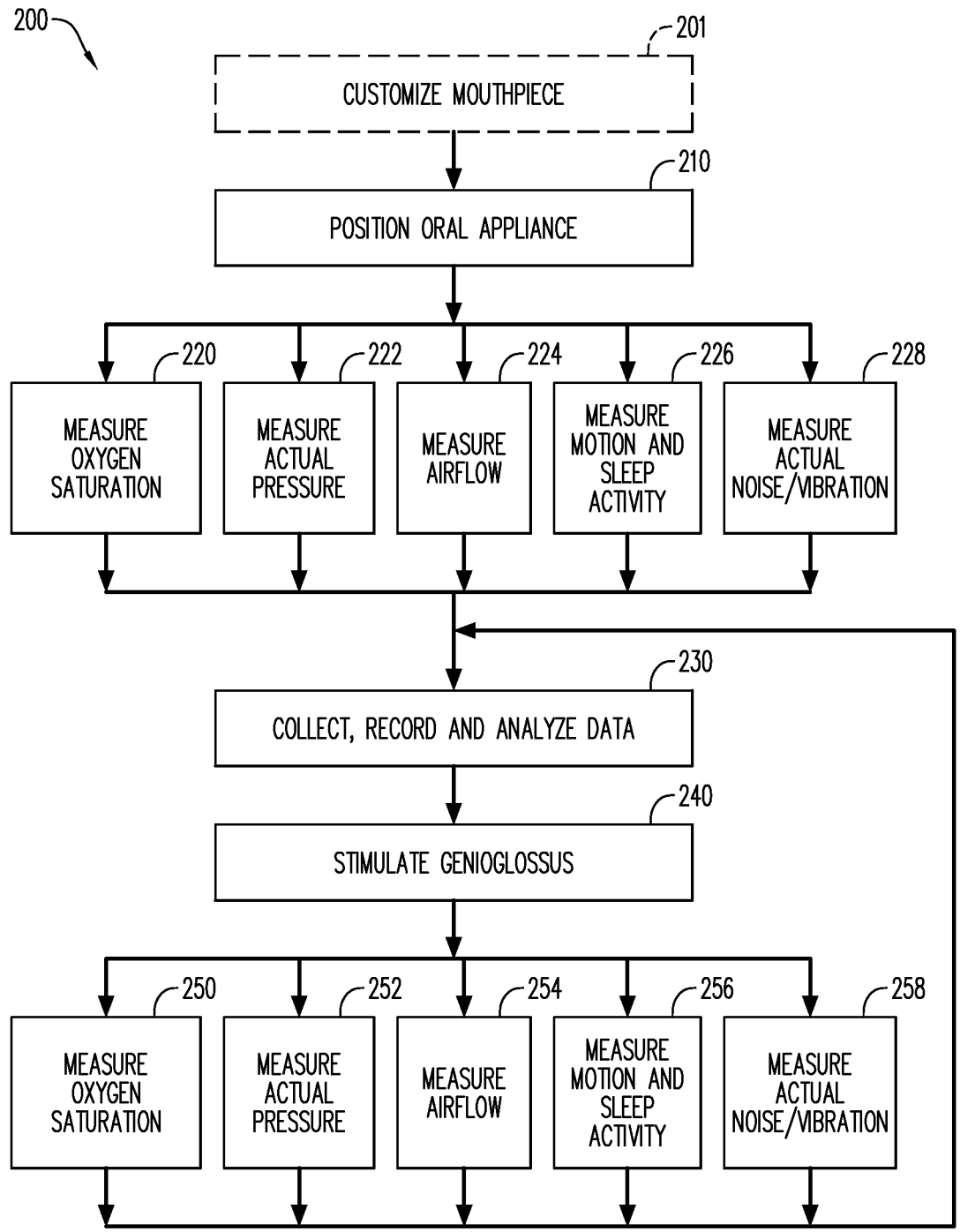
FIG. 6 is a schematic of a method for providing electrical genioglossus stimulation, according to an embodiment.

FIG. 6 is a flowchart illustrating an exemplary operation 200 of the oral appliance 10. Optionally, a customized mouthpiece is created 201 and various electronic components are assembled to form the oral appliance. The mouthpiece of the oral appliance is positioned 210 in the user's oral cavity. Oxygen sensors measure 220 oxygen saturation levels of the users hemoglobin, pressure sensors measure 222 the pressure applied to occlusal surfaces of the customized mandibular mouthpiece, airflow sensors measure 224 the actual airflow and/or breathing rate of the user, actigraphy sensors measure 226 data related to sleep activity, including sleep position and movement of the user during sleep and/or noise detectors measure 228 the actual noise and/or vibrations created by the user during sleep. The microprocessor collects, records and analyzes data 230 relating to oxygen saturation, pressure, airflow, sleep activity and actual noise levels. In the event that actual oxygen saturation levels of hemoglobin are below a predetermined level or in the event that the actual pressure applied to the occlusal portion of the mouthpiece is above the predetermined pressure level, the stimulator sends impulses 240 to stimulate the genioglossus muscle of the user's tongue. The oxygen sensors re-measure 250 the oxygen saturation level of hemoglobin, the pressure sensor re-measures 252 the pressure applied to occlusal surfaces of the customized mandibular mouthpiece, the airflow sensors re-measure 254 actual airflow of the user, the actigraphy sensors re-measure 256 the user's sleep activity, and the noise detector re-measures 258 the actual noise and/or vibrations created by the user during sleep. Stimulation is stopped if the predetermined levels are achieved. According to an aspect If the predetermined levels are not achieved, stimulation continues, increases, decreases or otherwise varies according to the measured values.

Figure 7:
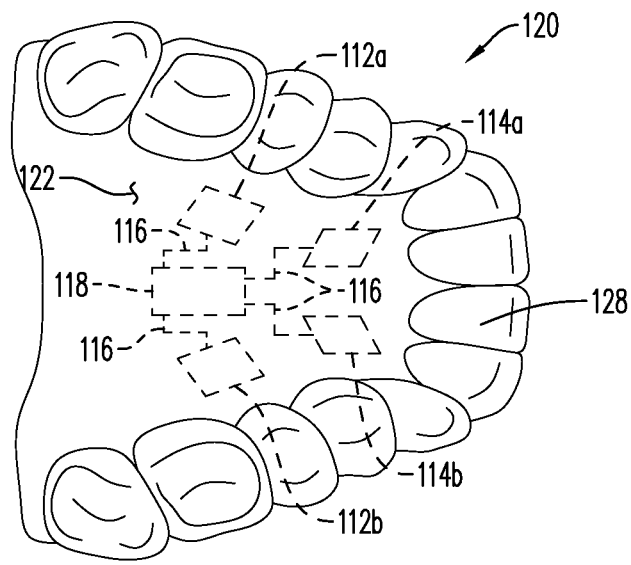
FIG. 7 is a bottom view of a top mouthpiece oral appliance, according to an embodiment.

According to an aspect, an upper mouthpiece 120 is configured to be secured to the user's upper dentition. As illustrated in FIG. 7, the mouthpiece 120 includes dentition attachment members 128 attached to and surrounding palate portion 122. The dentition attachment members 128 have a shape and size that substantially conforms to the upper dentition of the user. The palate portion 122 of the upper mouthpiece 120 substantially conforms to the palate of the user. Thus, the user is presented with a mouthpiece 120 having a secured and customized fit. The dentition attachment members 128 may be provided with a wire-frame form for support or, as shown in FIG. 7, support may stem from the presence of the palate portion 122 and the material chosen for forming the upper mouthpiece 120. According to an aspect, a portion of the dentition attachment members 128 may be shaped to form a retention loop around one or more teeth of the user. The dentition attachment members 128 and palate portion 122 render the upper mouthpiece 120 capable of being at least temporarily fixed in place by virtue of the customized fit. As such, the mouthpiece 120 may provide a retention function thereby allowing it to remain in place during the user's sleep, particularly in situations where the user may make slight to moderate movements during sleep and/or when the user may be awake.

Thus, the mouthpiece 120 may be substantially immovable unless positive effort is applied to remove the mouthpiece 120. In other words, the user may remove the mouthpiece 120 at any time, if desired, by exerting a little pressure to remove the mouthpiece 120. Since the mouthpiece 120 is not permanently affixed to the dentition, it can be worn and/or subsequently removed by the user at any time.

Figure 9:
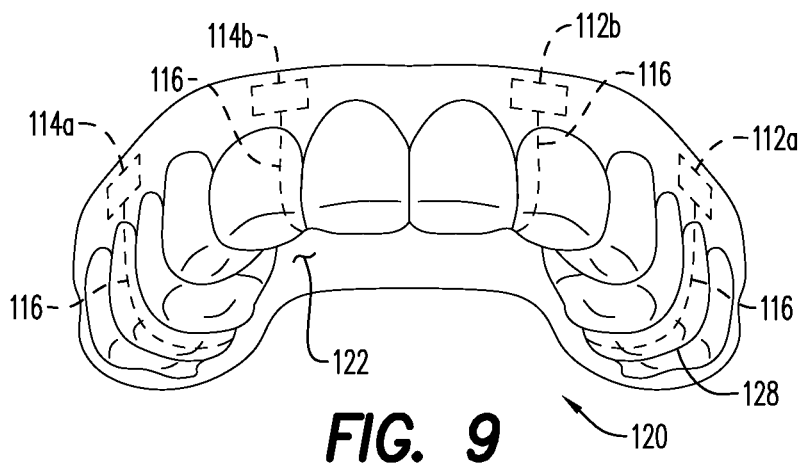
FIG. 9 is a bottom, anterior perspective view of the mouthpiece oral appliance, according to an embodiment.

As with mouthpiece 20, components may be positioned on and/or embedded within the upper mouthpiece 120. Components in or on the upper mouthpiece 120 may include any of the components associated with the mouthpiece 20. The components illustrated in FIG. 7 include a first pair of electrodes 112a, 112b, a second pair of electrodes 114a, 114b, a microprocessor 118 and electrical leads 116 connecting each electrode to the microprocessor 118. The microprocessor 118 may have a data recorder 60 and/or a battery 70 associated and integral therewith. portion that can If not embedded within the upper mouthpiece 120, any component on any surface of mouthpiece 120 is covered to eliminate tissue damage and damage to the components. Placement of the components should not interfere with the fit of the upper mouthpiece 120 in the user's mouth or irritate user's gums or palate. Electrical leads 116 are also either embedded in the material of the mouthpiece 120 or, if placed on the surface of the mouthpiece, covered to eliminate a number of readily apparent issues with loose leads. FIG. 9 illustrates how the electrical leads 116 follow the shape of the upper mouthpiece 120, either within or on top of the mouthpiece material, from each electrode to the microprocessor 118.

The microprocessor 118 of the upper mouthpiece 120 may also be provided with a wireless transceiver that enables it, like the oral appliance 10, to communicate with external wireless communication devices, such as, for example, computers, smart watches, smart phones, and the like. In addition, the wireless transceivers of the upper mouthpiece 120 and oral appliance 10 may communicate with one another. Thus, microprocessor 118 of the upper mouthpiece 120 may supply information to the oral appliance 10 is much the same way that the oral appliance receives information from external sources as well as its constituent components. Alternatively, it is contemplated that the upper mouthpiece 120 and oral appliance 10 may be wired together in a manner that would not be inconvenient or uncomfortable to the user.

FIG. 7 shows an arrangement where the first electrode pair 112a, 112b, the second electrode pair 114a, 114b and microprocessor 118 are all located in or on the palate portion 122 of the upper mouthpiece 120. Although there is ample room toward the posterior portion of the upper mouthpiece 120 palate portion 122, it may be difficult to obtain a strong electroencephalograph signal underneath the soft palate of the user while it is possible to obtain such a signal underneath the hard palate. Electrical leads 116 convey the electrical signals from each of the electrodes 112a, 112b, 114a, 114b to the microprocessor 118.

Figures 8A, 8B:
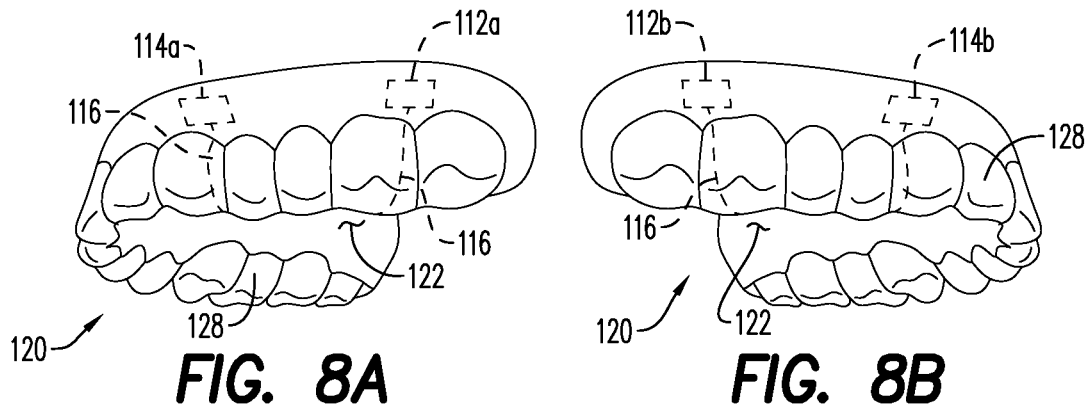
FIG. 8A is a bottom, left-side perspective view of the mouthpiece oral appliance, according to an embodiment.
FIG. 8B is a bottom, right-side perspective view of the mouthpiece oral appliance shown in FIG. 8A.

FIGS. 8A and 8B show an arrangement where the first electrode pair 112a, 112b and the second electrode pair 114a, 114b are located on the portion of upper mouthpiece 118 that is adjacent the buccal maxillary bone of the user. That is, the first electrode pair 112a, 112b and the second electrode pair 114a, 114b are located between the upper gums and inner lip/cheek of the user. Electrodes 112a and 114a are located on the left side of the buccal maxillary bone of the user and their paired electrodes 112b and 114b are located on the right side of the user's buccal maxillary bone. The locations of the electrodes in FIGS. 8A and 8B permit a good EEG signal, which can be clearly ready an interpreted, to be achieved by the electrodes and microprocessor 118. The microprocessor 118, though it cannot be seen in FIGS. 8A and 8B, may be located in or on the palate portion 122 of the upper mouthpiece 120, i.e., in approximately the same location on the palate portion 122 as in FIG. 7. Electrical leads 116 convey the electrical signals from each of the electrodes 112a, 112b, 114a, 114b to the microprocessor 118 by the most direct route along or within the material of upper mouthpiece 120. For example, the electrical leads 116 may follow the contour of the dentition attachment member 128 down, over and then up to the palate portion 122, where the electrical leads 116 then proceed to the microprocessor 118. The path of the electrical leads in FIGS. 8A and 8B are similar to those in FIG. 9, and FIG. 9 illustrates these paths more clearly.

FIG. 9 shows an arrangement where the first electrode pair 112a, 112b and the second electrode pair 114a, 114b are, like in FIGS. 8A and 8B, located on the portion of upper mouthpiece 118 that is adjacent the buccal maxillary bone of the user. Electrodes 112a and 114a are located on the posterior portion of the buccal maxillary bone of the user and their paired electrodes 112b and 114b are located on the anterior portion of the user's buccal maxillary bone. The locations of the electrodes in FIG. 9 permits a good EEG signal to be achieved by the electrodes and microprocessor 118. The microprocessor 118, though it cannot be seen in FIG. 9, is located in or on the palate portion 122 of the upper mouthpiece 120, i.e., in approximately the same location on the palate portion 122 as in FIG. 7. Electrical leads 116 convey the electrical signals from each of the electrodes 112a, 112b, 114a, 114b to the microprocessor 118 by the most direct route along or within the material of upper mouthpiece 120. That is, the electrical leads 116 will follow the contour of the dentition attachment member 128 down, over and then up to the palate portion 122, where the electrical leads 116 then proceed to the microprocessor 118.

With any of the electrode arrangements of electrodes shown in FIGS. 7, 8A, 8B and 9, each of first electrode pair 112a, 112b and second electrode pair 114a, 114b may, along with the microprocessor 118, comprise an electroencephalograph of sufficient sensitivity to detect rhythm changes in electrical signals in the brain. The electrodes 112a, 112b and 114a, 114b register voltage differences between the paired "a" electrode and "b" electrode generated by electrical signals in the brain. The signals detected by the electrodes are provided, via the electrical leads 116, to a signal processor that is part of the microprocessor 118.

As with any electroencephalograph, some mental/consciousness states result in the voltage differences detected between first electrode pair 112a, 112b and the second electrode pair 114a, 114b being rhythmic, shown as waves on a graph by the recording channel. The EEG signal for conscious adult in a relaxed state will typically be an oscillating wave known as an alpha wave. A sleeping adult's brain waves become extremely slow. These slow waves are referred to as delta waves and may be utilized not only to identify sleep but also to assess the depth of sleep. That is, varying strength of the delta waves can be indicative of a deeper sleep state. The signal processor and other microprocessor 118 components are able to differentiate various EEG rhythms and to determine, based on these detected rhythms, the various consciousness and sleep states of the user. It is contemplated that the mouthpiece 120 may be able diagnose epilepsy by way of recording the user's brain activity—such brain activity may be collected by the data recorder 60.

Figure 10:
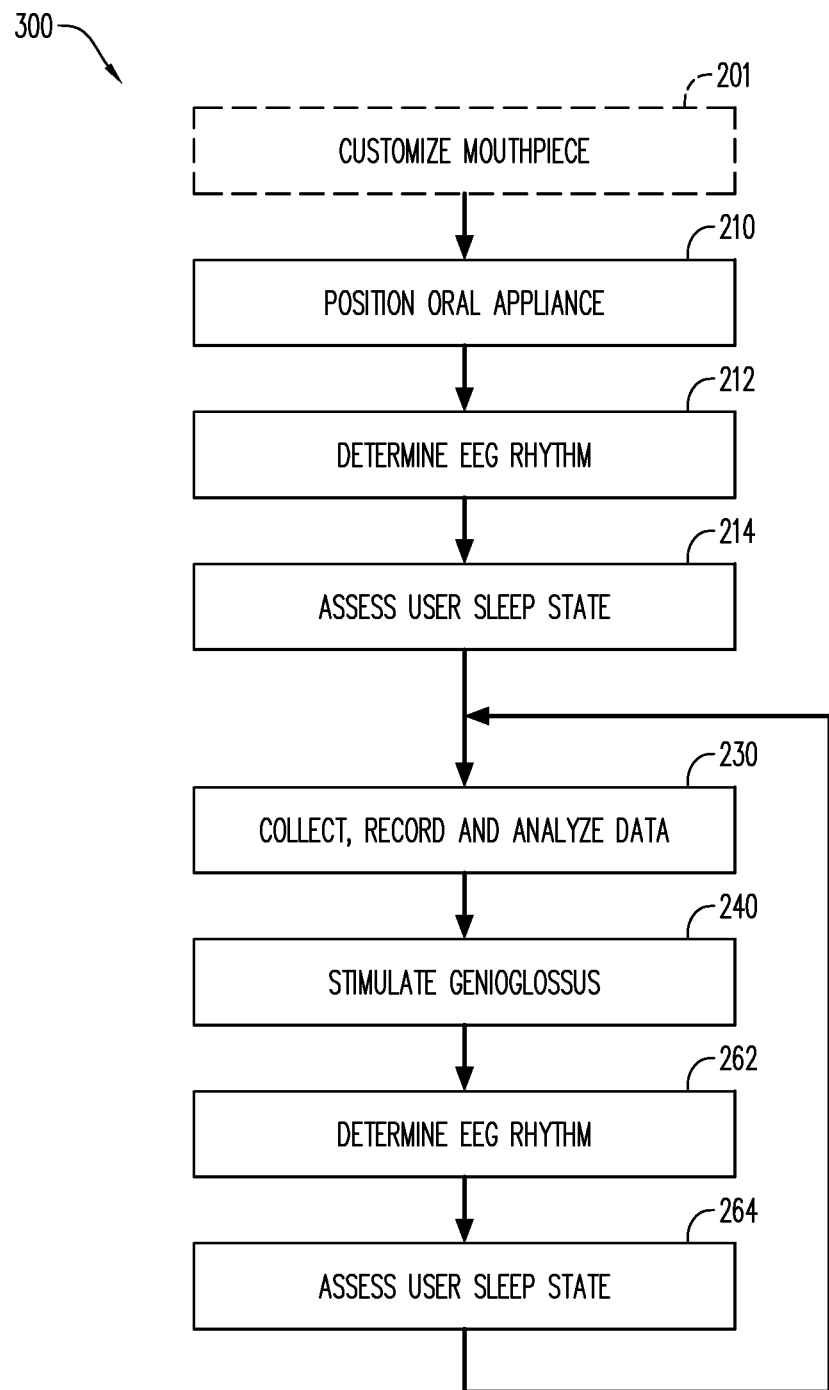
FIG. 10 is a schematic of a method for providing electrical genioglossus stimulation, according to an embodiment.

FIG. 10 is a flowchart illustrating an exemplary operation 300 of the upper mouthpiece 120 in cooperative communication with the oral appliance 10. Optionally, a customized upper mouthpiece 120 and oral appliance 10 mouthpiece are created 201 and various electronic components are assembled to form the full cooperative appliance. The upper mouthpiece 120 and mouthpiece portion of oral appliance 10 are positioned 210 in the user's oral cavity. The first electrode pair 112a, 112b and the second electrode pair 114a, 114b collect voltage data and the microprocessor assesses an EEG rhythm 212 from this data. The upper mouthpiece microprocessor 118 may utilize the EEG rhythm to assess the sleep state 214 of the user and a determination of sleep state is communicated to the oral appliance 10. Alternatively, the raw EEG rhythm may be communicated to the oral appliance 10 for assessment at step 230. In the event that the EEG data indicates that the user may be having an arousal from sleep or has exited a sleep state in an untimely manner, the microprocessor of the oral appliance may cause the stimulator to send impulses 240 to stimulate the genioglossus muscle of the user's tongue. The upper mouthpiece 120 is constantly assessing the EEG rhythms 262 and sleep state 264 of the user and providing data to the oral appliance. Stimulation is stopped if the appropriate sleep states are achieved. According to an aspect, if the predetermined EEG rhythms are not regained, stimulation continues, increases, decreases or otherwise varies according to the measured values.

The flowchart shown in FIG. 10 may be utilized independently of or in combination with the flowchart shown in FIG. 6. Thus, the EEG data may be used in combination with or supplemental to oxygen sensors measure 220, pressure sensors measure 222, airflow sensors measure 224, actigraphy sensors measure 226 and/or noise detectors measure 228.

The components of the apparatus illustrated are not limited to the specific embodiments described herein, but rather, features illustrated or described as part of one embodiment can be used on or in conjunction with other embodiments to yield yet a further embodiment. It is intended that the apparatus include such modifications and variations. Further, steps described in the method may be utilized independently and separately from other steps described herein.

While the apparatus and method have been described with reference to specific embodiments, it will be understood by those skilled in the art that various changes may be made and equivalents may be substituted for elements thereof without departing from the scope contemplated. In addition, many modifications may be made to adapt a particular situation or material to the teachings found herein without departing from the essential scope thereof.

In this specification and the claims that follow, reference will be made to a number of terms that have the following meanings. The singular forms "a," "an" and "the" include plural referents unless the context clearly dictates otherwise. Furthermore, references to "one embodiment", "some embodiments", "an embodiment" and the like are not intended to be interpreted as excluding the existence of additional embodiments that also incorporate the recited features. Approximating language, as used herein throughout the specification and claims, may be applied to modify any quantitative representation that could permissibly vary without resulting in a change in the basic function to which it is related. Accordingly, a value modified by a term such as "about" is not to be limited to the precise value specified. In some instances, the approximating language may correspond to the precision of an instrument for measuring the value. Terms such as "first," "second," "upper," "lower" etc. are used to identify one element from another, and unless otherwise specified are not meant to refer to a particular order or number of elements.

As used herein, the terms "may" and "may be" indicate a possibility of an occurrence within a set of circumstances; a possession of a specified property, characteristic or function; and/or qualify another verb by expressing one or more of an ability, capability, or possibility associated with the qualified verb. Accordingly, usage of "may" and "may be" indicates that a modified term is apparently appropriate, capable, or suitable for an indicated capacity, function, or usage, while taking into account that in some circumstances the modified term may sometimes not be appropriate, capable, or suitable. For example, in some circumstances an event or capacity can be expected, while in other circumstances the event or capacity cannot occur—this distinction is captured by the terms "may" and "may be."

As used in the claims, the word "comprises" and its grammatical variants logically also subtend and include phrases of varying and differing extent such as for example, but not limited thereto, "consisting essentially of" and "consisting of." Where necessary, ranges have been supplied, and those ranges are inclusive of all sub-ranges therebetween. It is to be expected that variations in these ranges will suggest themselves to a practitioner having ordinary skill in the art and, where not already dedicated to the public, the appended claims should cover those variations.

Advances in science and technology may make equivalents and substitutions possible that are not now contemplated by reason of the imprecision of language; these variations should be covered by the appended claims. This written description uses examples to disclose the method, machine and computer-readable medium, including the best mode, and also to enable any person of ordinary skill in the art to practice these, including making and using any devices or systems and performing any incorporated methods. The patentable scope thereof is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal language of the claims.

What is claimed is:

1. An oral appliance for treatment of sleep apnea in a user, comprising:
    a mouthpiece customized to a dentition of the user such that the mouthpiece is retained in an oral cavity of the user, wherein the mouthpiece comprises an upper portion and a lower portion;
    at least one microprocessor;
    a plurality of electrodes attached to the upper portion of the mouthpiece and electrically connected to the at least one microprocessor, wherein the plurality of electrodes and the at least one microprocessor are configured to determine electroencephalograph rhythms of a brain of the user;
    at least one sensor attached to the lower portion of the mouthpiece and configured to measure a relevant symptom of an immediate presence of sleep apnea in the user; and
    at least one stimulator attached to the lower portion of the mouthpiece, wherein the stimulator is configured to respond to the immediate presence of sleep apnea in the user by stimulating a genioglossus muscle of the user.

2. The oral appliance of claim 1, wherein the stimulator is an electrical stimulator configured to provide electrical stimulation to the genioglossus of the user.

3. The oral appliance of claim 1, further comprising:
    one or more reservoirs arranged on a lingual wall of the lower portion,
    each reservoir of the one or more reservoirs containing a pharmaceutical compound configured to stimulate the genioglossus by dispensing a portion of the pharmaceutical compound from the reservoir.

4. The oral appliance of claim 3, wherein the stimulator is an electrical stimulator configured to emit an electrical charge.

5. The oral appliance of claim 4, wherein the pharmaceutical compound bears a charge and each reservoir of the one or more reservoirs is semipermeable such that the electrical charge emitted by the stimulator results in the pharmaceutical compound migrating out of each reservoir of the one or more reservoirs and exposure of the user's oral tissue to the pharmaceutical compound.

6. The oral appliance of claim 4, wherein each reservoir of the one or more reservoirs is ruptured as a result of the stimulator emitting the electrical charge.

7. The oral appliance of claim 1, wherein the upper portion comprises:
a dentition attachment portion configured to conform to at least a portion of an upper dentition of the user; and,
a palate attachment portion configured to conform to at least a portion of a palate of the user.

8. The oral appliance of claim 7, wherein the plurality of electrodes and the at least one microprocessor are attached to the palate attachment portion.

9. The oral appliance of claim 7, wherein the plurality of electrodes are attached to the dentition attachment portion.

10. The oral appliance of claim 1, wherein the at least one sensor is an oxygen sensor.

11. A mouthpiece customizable to dentition of a user, comprising:
an upper mouthpiece configured to be retained on an upper dentition of the user, the upper mouthpiece having a lingual wall and a buccal wall;
a lower mouthpiece configured to be retained on a lower dentition of the user, the lower mouthpiece having a lingual wall and a buccal wall;
a plurality of electrodes attached to the upper mouthpiece, wherein the plurality of electrodes are configured to detect electrical rhythms from a brain of the user, the electrical rhythms being indicative of an immediate presence of sleep apnea in the user;
at least one sensor attached to the lower portion of the mouthpiece and configured to measure a relevant symptom to the immediate presence of sleep apnea in the user;
a microprocessor configured to receive signals from at least one of the at least one sensor and the plurality of electrodes, wherein the plurality of electrodes and microprocessor cumulatively operate as an electroencephalograph and detect electrical rhythms from the user's brain; and
at least one electrical stimulator attached to the lower mouthpiece,
wherein the stimulator is configured to emit an electrical current or field in response to the immediate presence of sleep apnea in the user based on at least one of the relevant symptom and the electrical rhythms from the user's brain.

12. The oral appliance of claim 11, further comprising:
a reservoir arranged on at least one of the lingual wall and the buccal wall of the lower mouthpiece, the reservoir containing a pharmaceutical compound configured to stimulate the genioglossus by dispensing a portion of the pharmaceutical compound from the reservoir.

13. The oral appliance of claim 12, wherein the pharmaceutical compound bears a charge and the reservoir is semipermeable such that the electrical current or field emitted by the stimulator results in the pharmaceutical compound migrating out of the reservoir and exposure of the oral tissue to the pharmaceutical compound.

14. The oral appliance of claim 12, wherein the reservoir is ruptured as a result of the stimulator emitting the electrical current or field.

15. The oral appliance of claim 11, wherein the upper portion further comprises:
a dentition attachment portion configured to conform to at least a portion of the upper dentition of the user; and,
a palate attachment portion configured to conform to at least a portion of a palate of the user.

16. The oral appliance of claim 15, wherein the plurality of electrodes and the microprocessor are attached to the palate attachment portion.

17. The oral appliance of claim 16, wherein at least one electrode of the plurality of electrodes are attached to the dentition attachment portion.

18. An oral appliance kit, comprising:
an oral appliance for treatment of sleep apnea in a user, the oral appliance comprising:
a mouthpiece customized to a dentition of the user such that the mouthpiece is retained in an oral cavity of the user, the mouthpiece comprising an upper portion and a lower portion;
at least one microprocessor;
a plurality of electrodes attached to the upper portion of the mouthpiece and electrically connected to the at least one a-microprocessor, wherein the plurality of electrodes and the at least one microprocessor are configured to measure electroencephalograph rhythms indicative of an immediate presence of sleep apnea in the user;
at least one sensor attached to the lower portion of the mouthpiece and configured to measure oxygen levels indicative of the immediate presence of sleep apnea in the user;
at least one stimulator attached to the lower portion of the mouthpiece, wherein the at least one stimulator is configured to emit an electrical current or field in response to the immediate presence of sleep apnea in the user based on at least one of the electroencephalograph rhythms and the oxygen levels; and
a rechargeable battery attached to the upper portion of the mouthpiece or the lower portion of the mouthpiece, the rechargeable battery configured to provide power to the at least one microprocessor, the at least one sensor, the plurality of electrodes, and the at least one stimulator.

19. The oral appliance kit of claim 18, wherein the mouthpiece further comprises:
one or more reservoirs arranged on at least one of a lingual wall and a buccal wall of the lower portion of the mouthpiece, each reservoir of the one or more reservoirs containing a pharmaceutical compound configured to stimulate a genioglossus muscle of the user by dispensing a portion of the pharmaceutical compound from each reservoir of the one or more reservoirs.

20. The oral appliance kit of claim 19, wherein each reservoir of the one or more reservoirs is ruptured as a result of the at least one stimulator emitting the electrical current or field such that the pharmaceutical compound migrates out of each reservoir of the one or more reservoirs and exposes an oral tissue of the user to the pharmaceutical compound.

* * * * *

UNITED STATES PATENT AND TRADEMARK OFFICE
CERTIFICATE OF CORRECTION

PATENT NO. : 11,234,638 B2
APPLICATION NO. : 16/673077
DATED : February 1, 2022
INVENTOR(S) : Reza Radmand It is certified that error appears in the above-identified patent and that said Letters Patent is hereby corrected as shown below:

In the Claims

Column 22, Line 26, delete "a"

Signed and Sealed this
Twenty-eighth Day of June, 2022

Katherine Kelly Vidal
*Director of the United States Patent and Trademark Office*